United States Patent
An et al.

(10) Patent No.: US 7,648,529 B2
(45) Date of Patent: Jan. 19, 2010

(54) TELESCOPING SPINAL IMPLANT

(75) Inventors: Howard An, Riverwoods, IL (US); Yves Crozet, Bellach (CH); Todd Harrington, Golden, CO (US)

(73) Assignee: Stryker Spine (FR)

( * ) Notice: Subject to any disclaimer, the term of this patent is extended or adjusted under 35 U.S.C. 154(b) by 855 days.

(21) Appl. No.: 11/010,496

(22) Filed: Dec. 13, 2004

(65) Prior Publication Data

US 2005/0113921 A1 May 26, 2005

Related U.S. Application Data

(63) Continuation of application No. 09/388,726, filed on Sep. 2, 1999, now Pat. No. 6,866,682.

(51) Int. Cl.
*A61F 2/44* (2006.01)

(52) U.S. Cl. .................................. 623/17.15; 606/105

(58) Field of Classification Search .................. 606/251, 606/150, 90, 105, 262, 320; 623/17.15; 74/89.12, 575, 578; 411/81, 109, 118, 190, 411/199, 200, 205, 209; 81/319, 320, 10, 81/482

See application file for complete search history.

(56) References Cited

U.S. PATENT DOCUMENTS

| | | |
|---|---|---|
| 4,401,112 A | 8/1983 | Rezaian |
| 4,553,273 A | 11/1985 | Wu |
| 4,657,550 A | 4/1987 | Daher |
| 4,880,343 A | 11/1989 | Matsumoto |
| 4,932,975 A | 6/1990 | Main et al. |
| 5,171,278 A | 12/1992 | Pisharodi |
| 5,192,327 A | 3/1993 | Brantigan |
| 5,236,460 A | 8/1993 | Barber |
| 5,290,312 A | 3/1994 | Kojimoto et al. |
| 5,306,310 A | 4/1994 | Siebels |
| 5,336,223 A | 8/1994 | Rogers |
| 5,390,683 A | 2/1995 | Pisharodi |
| 5,413,602 A | 5/1995 | Metz-Stavenhagen |
| 5,429,447 A | 7/1995 | Wood |
| 5,431,658 A | 7/1995 | Moskovich |
| 5,482,417 A | 1/1996 | Erickson |

(Continued)

FOREIGN PATENT DOCUMENTS

DE    3023942 A1    1/1982

(Continued)

OTHER PUBLICATIONS

The DePuy Motech Surgical Titanium Mesh Catalogue, 1994 DePuy Motech, Inc.

*Primary Examiner*—Brian E. Pellegrino
(74) *Attorney, Agent, or Firm*—Lerner, David, Littenberg, Krumholz & Mentlik, LLP

(57) ABSTRACT

A corpectomy device has an inner member telescopingly disposed in an outer member so that the inner member is movable in an axial direction. The inner and outer members are hollow, defining a chamber, and include apertures in communication with the chamber. A locking clip engages the inner and outer members to fix the position of the inner member with respect to the outer member. The longitudinal dimension of the device is adjustable by distracting the inner member so that the inner member extends from the outer member and moving the locking clip from an unlocked position to a locked position.

5 Claims, 8 Drawing Sheets

U.S. PATENT DOCUMENTS

| | | |
|---|---|---|
| 5,522,899 A | 6/1996 | Michelson |
| 5,549,608 A | 8/1996 | Errico et al. |
| 5,571,192 A | 11/1996 | Schönhöffer |
| 5,575,790 A | 11/1996 | Chen et al. |
| 5,591,235 A | 1/1997 | Kuslich |
| 5,693,100 A | 12/1997 | Pisharodi |
| 5,702,449 A | 12/1997 | McKay |
| 5,702,453 A | 12/1997 | Rabbe et al. |
| 5,702,455 A | 12/1997 | Saggar |
| 5,720,746 A | 2/1998 | Soubeiran |
| 5,723,013 A | 3/1998 | Jeanson et al. |
| 5,776,197 A | 7/1998 | Rabbe et al. |
| 5,776,198 A | 7/1998 | Rabbe et al. |
| 5,989,290 A | 11/1999 | Biedermann |
| 6,015,436 A | 1/2000 | Schonhoffer |
| 6,177,883 B1 | 1/2001 | Jennetti et al. |
| 6,190,413 B1 | 2/2001 | Sutcliffe |
| 6,193,756 B1 | 2/2001 | Studer et al. |
| 6,200,348 B1 | 3/2001 | Biedermann et al. |
| 6,524,341 B2 | 2/2003 | Lang et al. |

FOREIGN PATENT DOCUMENTS

| | | |
|---|---|---|
| DE | 4012622 C1 | 7/1991 |
| DE | 19604246 A1 | 8/1996 |
| DE | 19509317 A1 | 9/1996 |
| DE | 195 19 101 A1 | 11/1996 |
| DE | 19622827 A1 | 12/1997 |
| DE | 29/616778 | 3/1998 |
| EP | 0 188 954 | 7/1986 |
| EP | 0 307 741 B1 | 3/1989 |
| EP | 0 567 424 A1 | 10/1993 |
| EP | 0 637 440 A1 | 8/1994 |
| FR | 2 636 227 | 3/1990 |
| JP | 62-164458 | 7/1987 |
| JP | 2261446 | 10/1990 |
| WO | WO-92/01428 | 2/1992 |
| WO | WO-94/18913 | 9/1994 |
| WO | WO-95/26164 | 10/1995 |
| WO | WO-96/17564 | 6/1996 |
| WO | WO-96 37170 A1 | 11/1996 |
| WO | WO-97/00054 | 1/1997 |
| WO | WO-97 47258 A1 | 12/1997 |
| WO | WO-98/46173 | 10/1998 |
| WO | WO-98 46173 A1 | 10/1998 |
| WO | WO-00 23013 | 4/2000 |

TELESCOPING SPINAL IMPLANT

CROSS-REFERENCE TO RELATED APPLICATIONS

This application is a continuation of application Ser. No. 09/388,726 filed Sep. 2, 1999, the disclosure of which is hereby incorporated by reference herein.

BACKGROUND OF THE INVENTION

The present invention relates to devices used to support the spine after removal of at least a part of a vertebra.

When a vertebra becomes damaged or diseased, surgery may be used to replace the vertebra or a portion thereof with a prosthetic device for maintaining the normal spacing of the vertebrae and to support the spine. The prosthesis, which may be referred to as a corpectomy device, is inserted into the cavity created when the vertebra was removed. One such device disclosed by Saggar, U.S. Pat. No. 5,702,455 includes a pair of cylindrical hollow members which are internally threaded and interact with a central cylindrical jacking screw which is externally threaded. The top part of the jacking screw is threaded in an opposite direction from a bottom part of the jacking screw. The jacking screw may be engaged and turned to adjust the vertical dimension of the device. When the jacking screw is turned, the hollow cylinders move either toward each other or away from each other.

Another prosthesis disclosed by U.S. Pat. No. 5,290,312 to Kojimoto et al. has two hollow rectangular cylinders. Each cylindrical part has at least one open end. The tubular parts are sized and shaped so that one part is telescopingly received in the other. The position of the parts in relation to each other are fixed by one or more set screws passed through apertures in one part to engage the other part. A corpectomy prosthesis disclosed by International Publication No. WO 92/01428 of Rasheed includes two parts, each having toothed surfaces. The position of the parts are fixed in relation to each other by the interengagement of the toothed surfaces.

Prostheses for supporting the spine after removal of a vertebra or a portion of a vertebra are desirably adjustable according to the size of the cavity created by the corpectomy procedure. The size of the cavity will depend upon the size of the particular patient, and the location of the cavity along the spine. In addition, the device may be adjusted either prior to insertion into the cavity or in situ within the cavity. For devices adjusted in situ, a convenient means for locking the device in the correct height is desirable. Although the patents discussed above present various solutions, further improvement in this area would be desirable.

SUMMARY OF THE INVENTION

The present invention addresses these needs.

One aspect of the present invention provides a corpectomy device comprising a first member having a longitudinal axis, a second member moveable in an axial direction with respect to the first member, and a locking clip engagable with the first member and the second member and moveable between a first position and a second position for locking the first member and second member in a relative axial position with respect to one another. The corpectomy device has a locking clip so that the device may be positioned within the cavity created during the corpectomy procedure, distracted in situ, and locked in place. The device is adjustable to engage adjacent vertebrae while the locking clip is in an unlocked position. After adjustment, the locking clip may be moved to the locked position so that the device supports the spine.

In certain preferred embodiments, the second member includes at least one ridge and the locking clip includes at least one depression for locking the device. The at least one ridge is engaged in the at least one depression so that the locking clip engages the second member. In preferred embodiments, the locking clip and the second member include interengaging threads.

The locking clip may be mounted on the device in a number of ways. The locking clip may be rotatably movable between locked and unlocked positions, or otherwise movably mounted on the first member. The locking clip may be translatably moveable between locked and unlocked positions. The locking clip preferably includes a first bore and the first member preferably includes a corresponding hole. The first bore and the hole are engagable by a member, such as a set screw, for locking the position of the locking clip in its locked position.

The second member may be telescopingly received in the first member. It is preferable that at least one of the first member and second member comprises a hollow member, the first member and the second member defining a chamber therebetween. It is also preferable that at least one of the first member and second member include perforations for permitting the ingrowth of bone, blood vessels, and other tissue. These perforations preferably include elongated perforations extending in the axial direction on one of the first member and the second member and substantially circular perforations on the other of the first member and the second member. At least one aperture is desirable for providing access to the chamber so that the device may be packed with fragments of bone, bone growth factors, or other material encouraging the growth of bone, blood vessels and other tissue, after being mounted within a patient. This aperture may also be used to fill the chamber with bone cement or other materials used in the procedure. Other perforations may be provided in sizes and shapes for encouraging ingrowth of tissue.

The corpectomy device preferably includes outwardly extending flanges on outer axial ends of the second member and the first member. The flanges preferably include teeth so that the adjacent vertebrae may be engaged by the teeth, securing the device in the spine. The flanges are disposed at an acute angle, in certain preferred embodiments, with respect to the common longitudinal axis of the first member and the second member. The angled flanges adapt to differences in the curvature of different sections of the spine. The particular angles generally will depend upon the position of the device within the spine.

The second member may comprise an inner tubular member and the first member may comprise an outer tubular member having a passage extending therethrough. The passage may be polygonal in shape and centrally located in the outer tubular member. The passage engages the inner tubular member so that the inner tubular member is telescopingly received in the outer tubular member.

The locking clip may engage the outer tubular member via a wedge on the locking clip. The outer tubular member may include a hole and the wedge on the locking clip would be engagable in the hole so that the locking clip engages the outer tubular member. To engage the inner tubular member and lock the device, the wedge may include a depression and the inner tubular member may include at least one bridge portion to be engaged in the depression.

The tubular cross-sectional shapes of the outer tubular member, inner tubular member and locking clip include various shapes. The passage of the outer tubular member has a cross-sectional shape which at least partially corresponds to the cross-sectional shape of the inner tubular member so that the inner tubular member is telescopingly received in the passage. The tubular members may have an exterior surface defining a different shape than an exterior surface of the tubular members. The cross-sectional shape of the inner tubular member and the passage may be, for example, substantially square. However, the cross-sectional shape of the inner tubular member and the passage may also be triangular, that of a parallelopiped, elliptical, circular or other geometrical shapes. Non-circular shapes are preferred to prevent the inner tubular member from rotating with respect to the outer tubular member. The outer tubular member may include a wall having an inner surface defining the passage. The outer tubular member may also include an outer surface defining a cross-sectional shape different from the cross-sectional shape of the inner tubular member and the passage. The outer surface, for example, may define a cross-sectional shape of a square, triangle, parallelopiped, ellipse, circle, or other shapes.

Interrupted threads, grooves or ridges in mating surfaces of the locking clip and the inner tubular member may be used to lock the relative position of the inner and outer tubular member. The inner tubular member has an outer surface which may include first surface portions and second surface portions. An inner surface of the locking clip defines an aperture and may include third surface portions and fourth surface portions. The third surface portions are shaped to correspond to the first surface portions on the inner tubular member so that the inner tubular member is telescopingly received in the passage when the locking clip is in its unlocked position. The third and fourth surface portions are preferably curvilinear in shape and have different radii of curvature. The outer surface of the inner tubular member may define a substantially square cross-sectional shape, including rounded corners comprising the first surface portions and sides comprising the second surface portions. The inner surface of the locking clip includes circular surface portions comprising the fourth surface portions and rounded corners comprising the third surface portions. The rounded corners on the inner tubular member and the locking clip are in alignment when the locking clip is in its unlocked position. The circular surface portions may have ridges for engaging ridges on the rounded corners of the inner tubular member when the locking clip is in its locked position. In preferred embodiments, the circular surface portions on the locking clip and rounded corners of the inner tubular member have interengaging threads.

The corpectomy device may also comprise an inner member having a polygonal shape including corners, an outer member having a polygonal passage sized and shaped so that the inner member is telescopingly and non-rotatably received in the outer member so that inner member and the outer member have a longitudinal axis. The device also has a removable locking clip having an inner surface defining an aperture including corners and locking portions. The locking clip is rotatably mounted on the outer member so that the locking clip is limited in axial movement on the outer member. Mating surfaces on the locking portions and the corners on the inner member engage each other to prevent axial movement between the locking clip and the inner member.

The mating surfaces comprise, in preferred embodiments, threads on the locking portions of the locking clip and the corners of the inner member. The outer member may include a slot and the locking clip may include a pin mounted on the locking clip and extending through the slot to limit the axial movement of the locking clip. The pin may also be mounted so as to limit the rotational movement of the locking clip so that the clip is not rotated from an unlocked position, to a locked position, and then to a further unlocked position.

The outer member may include a hole and the locking clip may include a corresponding hole so that the holes may be engaged with a set screw for fixing the relative position of the locking clip with respect to the outer member. The inner member and outer member preferably each include a radially extending flange on an outer axial end of the inner member and the outer member. Most preferably, the flanges include teeth for engaging bone, especially the vertebrae adjacent the cavity formed during the corpectomy procedure. The flanges are, in some preferred embodiments, disposed at an acute angle with respect to the longitudinal axis of the device to restore the curvature of the spine after the corpectomy device is installed.

Another aspect of the invention provides a method of providing support to the spine of a patient after a cavity is created in the spine by removing at least a portion of a vertebra or vertebrae, comprising inserting into the cavity an adjustable corpectomy device including an outer member having a longitudinal axis, an inner member movable in an axial direction with respect to the outer member, and a locking clip for locking the relative position of the inner and outer members with respect to one another. The method includes distracting the corpectomy device by moving the inner and outer members with respect to each other to increase the longitudinal dimension of the device to an appropriate size for supporting the spine, and moving the locking clip to a locked position to fix the relative position of the inner and outer members with respect to each other. The method also comprises packing a hollow chamber in the corpectomy device with materials for the encouraging the ingrowth of bone, blood vessels, and other tissue. The step of distracting may include inserting a first end and a second end of a distraction device into corresponding holes in the inner and outer members, and moving the first and second ends to move the inner and outer members in an axial direction away from each other.

The step of moving the locking clip preferably includes engaging the locking clip with the inner member. The step of moving the locking clip may include rotating the locking clip or snapping the locking clip into engagement with an inner member. The method may also include inserting a set screw into a hole in the locking clip and twisting the set screw until the set screw engages another hole in the outer member, at least one of the holes being threaded to receive the set screw.

BRIEF DESCRIPTION OF THE DRAWINGS

These and other features, aspects and advantages of the present invention will become better understood with regard to the following description, appended claims and accompanying drawings where:

DETAILED DESCRIPTION OF THE DRAWINGS

Figure 1:
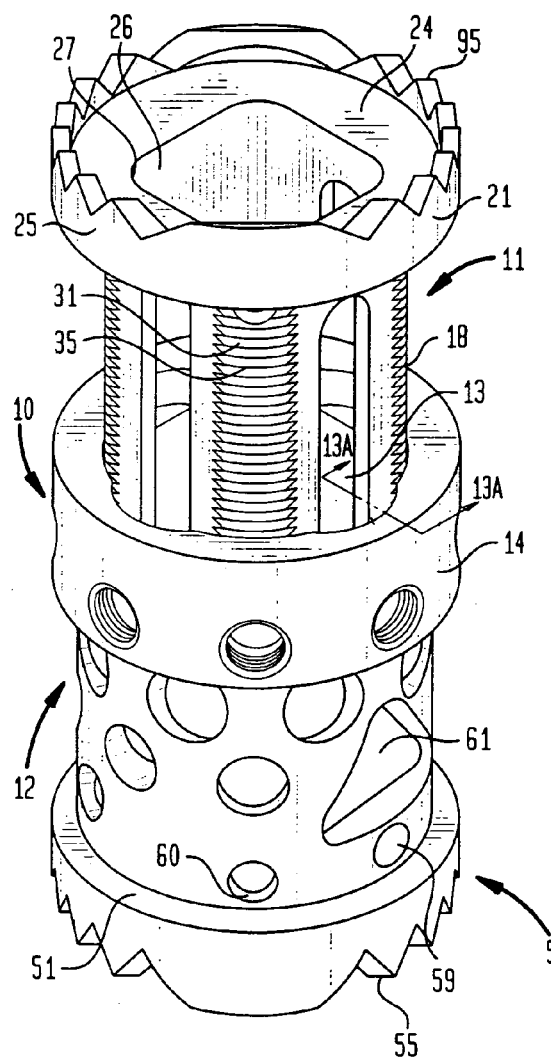
FIG. 1 is a perspective view of a corpectomy device in accordance with an embodiment of the invention.

Referring to FIG. 1, there is shown a corpectomy device 10 comprising an inner member 11 which may be cylindrical in shape or may have any polygonal cross-section, telescopingly received in an outer member 12 which may also be a cylinder. The device further includes a locking clip 14 having a locked position and an unlocked position, the locking clip being engagable with the inner member and the outer member for locking the inner member and the outer member in a relative position with respect to one another in a manner described in detail below.

Referring to FIGS. 1-3A, the inner member 11 has a top end 15 and a bottom end 16 and is essentially comprised of a wall 17 extending between ends 15 and 16 and defining a hollow tubular part 18 having an inner surface 19 and an outer surface 20. In the preferred embodiment, a top end 15 is generally circular and the cross-section of part 18 is generally square with outer rounded corners 31. Top end 15 has a circular base 24 and also includes an aperture 26 in the center of circular base 24. Aperture 26 is generally square in shape, and has rounded corners 27. Inner surface 19 of wall 17 defines a hollow space 30. Hollow space 30 extends from bottom end 16 of inner member 11 to aperture 26 in circular base 24. The inner hollow space is essentially square having rounded corners 37 defined by rounded corners 31 of wall 17.

Figure 2:
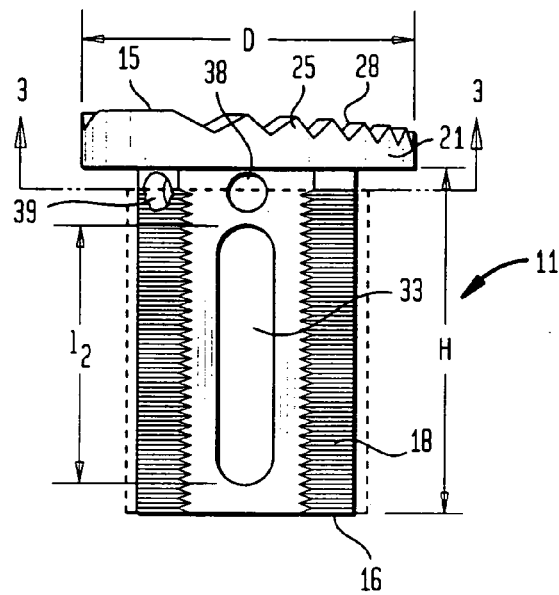
FIG. 2 is a front elevational view of an inner member of the corpectomy device of FIG. 1.

The outer surface 20 of wall 17 defines different surface portions. In the preferred embodiment, the outer surface 20 includes first surface portions having rounded corners 31 and second surface portions comprising sides 32 of the generally square cross-section. Rounded corners 31 of wall 17 have ridges 35 on outer surface 20. Sides 32 join adjacent rounded corners 31 of the wall 17. In the preferred embodiment, and as best seen in FIG. 2, sides 32 have orifices 33 which are elongated and extend in an axial direction in wall 17 of inner member 11. Orifices 33 communicate with hollow space 30.

Top 15 is preferably in the form of a flange 21 connected to or integral with tubular part 18, so that tubular part 18 extends from the bottom end 16 to the underside of flange 21. As best seen in FIG. 3A, flange 21 includes circular base 24 and preferably includes a peripheral extension, or wall 25, extending outwardly from circular base 24 with teeth 28 for engaging vertebrae adjacent a cavity within the spine.

Holes are provided in the inner cylinder adjacent the flange 21. At least one hole 38 is provided in a side 32 of wall 17 and at least one other hole 39 is provided in at least one corner 31 of wall 17. These holes are preferably provided so that they may be engaged by an instrument for distracting corpectomy device 10, as will be further explained below.

The dimensions of an inner member for a corpectomy device in accordance with the invention may be as follows, although the dimensions of the embodiment shown in the figures are not critical to the invention.

Figure 3:
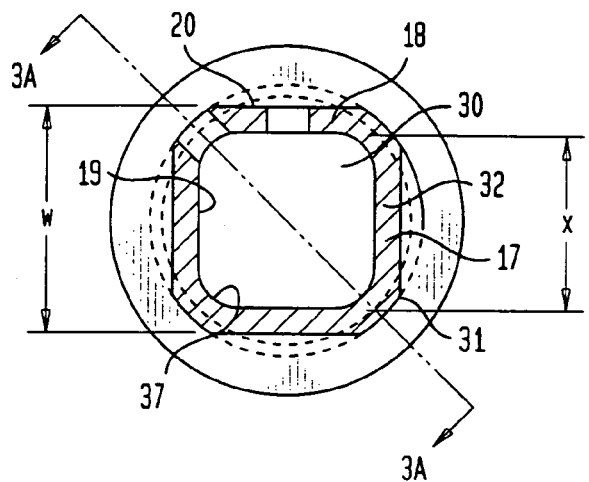
FIG. 3 is a cross-sectional view taken along line 3-3 in FIG. 2.
Figure 3A:
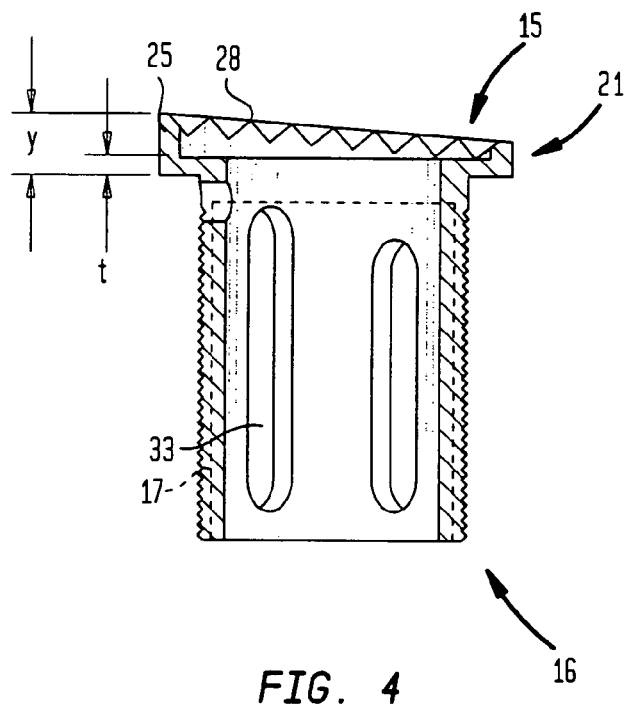
FIG. 3A is a cross-sectional view taken along line 3A-3A in FIG. 3.
Figure 4:
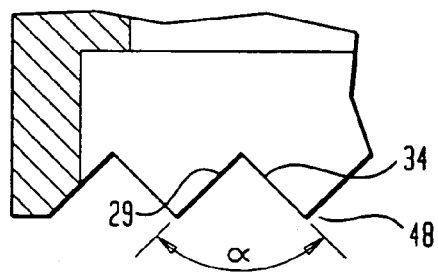
FIG. 4 is an inverted, partial detail of the flange of the inner cylinder of the corpectomy device of FIGS. 1-3A.
Figure 5:
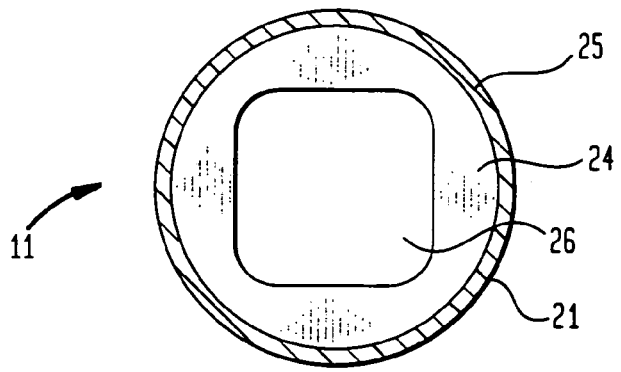
FIG. 5 is a top view of the inner member of the corpectomy device shown in FIGS. 1-4.

As best seen in FIG. 3A, wall 25 has a height y of about 6 mm and circular base 24 has a thickness t of about 2 mm. Each of teeth 28, as best seen in FIG. 4, is comprised of two adjacent surfaces extending in a direction away from base 24. Surfaces 29, 34 are disposed at an angle with respect to each other. The surfaces 29 and 34 define an angle α, which is preferably 90°. Each tooth has an apex 48 and the distance between adjacent apexes is about 4 mm. The extension 25 and teeth 28 form an angled toothed surface which, in the embodiment shown, is angled from the horizontal by 4°. This angle preferably varies, depending upon the application, as discussed below.

In the preferred embodiment, and as seen in FIGS. 2 and 3, the tubular part 18 of inner member 11 has a height H of about 36 mm. The preferred square tubular part has an exterior width W of about 22 mm, measured across the tube from outer surface 20 at one side 32 thereof to outer surface 20 of an opposite side 32. An inner width X is about 17 mm, measured from the inner surface 19 of one side 32 to inner surface 19 of an opposite side 32. This dimension of course may vary with the wall thickness. Rounded corners 31 on the substantially square part 18 are defined by a circle having diameter of 4 millimeters (mm). The ridges 35 are formed by recesses in rounded corners 31 and preferably comprise a left-handed thread such as a metric M26×1 thread. A person of ordinary skill may easily convert this designation to a thread based upon the U.S. system of dimensions.

Figure 2A:
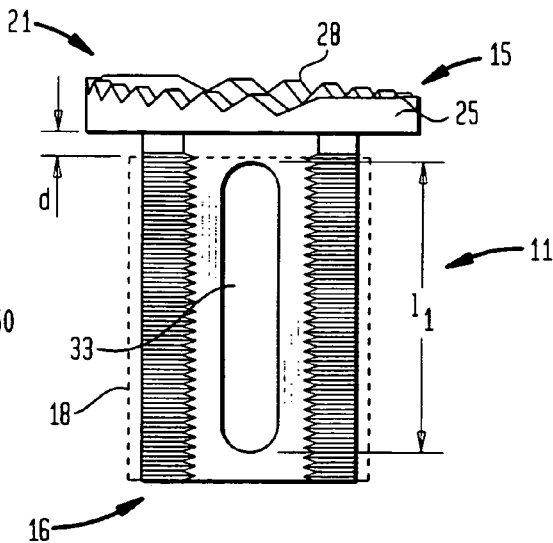
FIG. 2A is a rear elevational view of an inner member of the corpectomy device of FIGS. 1-2.

Orifices or slots 33 in sides 32 of the part 18 have a height $l_1$ of about 30 mm and are spaced from the base of flange 21 a distance of about 2.5 mm (distance d shown on FIG. 2A). The orifice 33 adjacent hole 38 has a height $l_2$ of about 27 mm to accommodate hole 38 located underneath the base of flange 21, as shown in FIG. 2.

Figure 6:
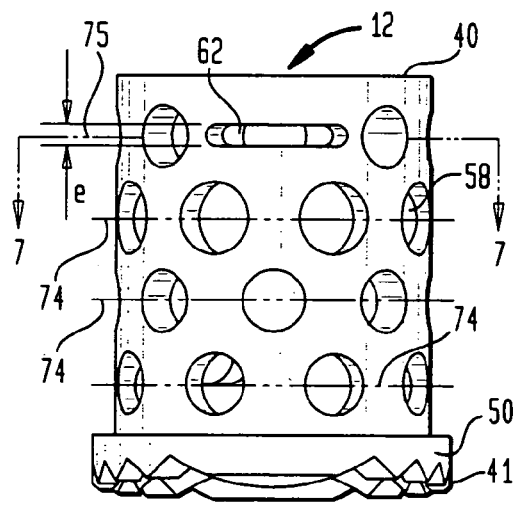
FIG. 6 is a right side elevational view of the outer member of the embodiment of FIGS. 1-5.
Figure 7:
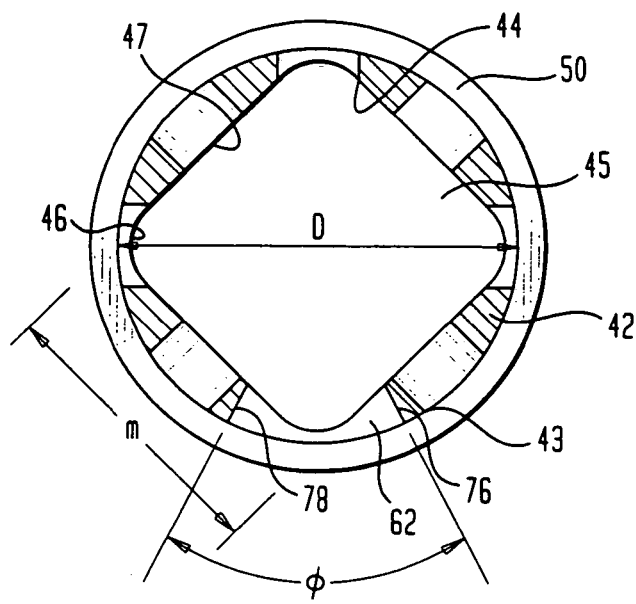
FIG. 7 is a cross-sectional view taken along line 7-7 in FIG. 6.

Referring to FIGS. 1 and 6-7 there is shown outer member 12 having an upper end 40 and a lower end 41. The outer member 12 includes a wall 42 having an outer surface 43 and an inner surface 44. In the preferred embodiment, an outer surface 43 defines a circular cross-section for the outer member 12, while inner surface 44 defines a substantially square cross-sectional shape for passage 45, extending from the upper end 40 to the lower end 41 and sized to receive part 18 of inner member 11. Passage 45 may be centrally located within the outer member and has rounded corners 46 defined by the inner surface 44 of wall 42. Passage 45 also has sides 47 also defined by the inner surface of wall 42 and extending between the rounded corners 46. The rounded corners 46 are shaped to correspond to rounded corners 31 of inner member 11, while the sides 47 are shaped to correspond to sides 32 of inner member 11 so that inner member 11 is telescopingly received in passage 45 of outer member 12.

A flange 50 is disposed at lower end 41 of outer member 12. The flange 50 is constructed similarly to the flange 21 of member 11. In the preferred embodiment, both flange 21 and flange 50 have a diameter D of about 34 mm. Like top flange 21, flange 50 has a circular base 51 and an inner aperture 52 with corners 53. Flange 50 also preferably includes an outwardly extending peripheral wall 54 with teeth 55 in an outer surface of wall 54 for engaging the vertebrae adjacent flange 50. Apertures 26 and 52 allow ingrowth of bone, blood vessels and other tissue from the vertebrae adjacent to flange 21 and flange 50. The peripheral wall 54 and teeth 55 also form an angled toothed surface having the same or different angle from that of flange 21.

Outer member 12 has orifices 58, defined by wall 42, as seen in FIGS. 1, 6, 6A, and 7. Orifices 58 extend from outer surface 43 to inner surface 44, communicating with passage 45. The orifices 58 allow the ingrowth of bone, blood vessels, and other tissue into the corpectomy device after the corpectomy device 10 is installed in a patient. The outer member 12 also includes holes 59 and 60, which correspond with holes 38 and 39 on inner member 11, for distracting the corpectomy device 10. Holes 59 and 60 extend through wall 42 and are located adjacent lower flange 50. Outer member 12 also preferably includes an aperture 61 which is located in wall 42 to provide access to passage 45 from the exterior of the corpectomy device 10. Through aperture 61, passage 45 may be packed with bone cement, which may be used to fix the device, although bone cement is not required. Aperture 61 may also be used to pack into the device chips of bone, materials for fixing the corpectomy device in the patient's body, or materials promoting the growth of bone, blood vessels, and other tissue. In the preferred embodiment, aperture 61 has a height f of about 12 mm. Preferably, a slit 62 in wall 42 of the outer member 12 extends from the outer surface 43 to the inner surface 44 and is elongated in a circumferential direction for moveably mounting the locking clip on the outer cylinder. Slit 62 has a first side 78 and a second side 76, both formed by wall 42. The preferred slit 62 has a height e of about 2 mm and a central horizontal plane 75 which is spaced about 6 mm from upper end 40. The preferred circumferential angle, $\phi$, between first side 78 and second side 76 is 53°.

The preferred outer member 12 has a height k of about 35 mm measured from the upper end 40 to flange 50. Flange 50 has dimensions which are the same as flange 21. Generally square passage 45 has a width m of about 22 mm, measured from the inner surface 44 of a side 47 to the inner surface of an opposite side 47. Rounded corners 46 are defined by the same radius as rounded corners 31 on inner member 11. Outer surface 43 defines a circular cross-sectional shape having a preferred diameter B of about 30 mm.

Figure 6A:
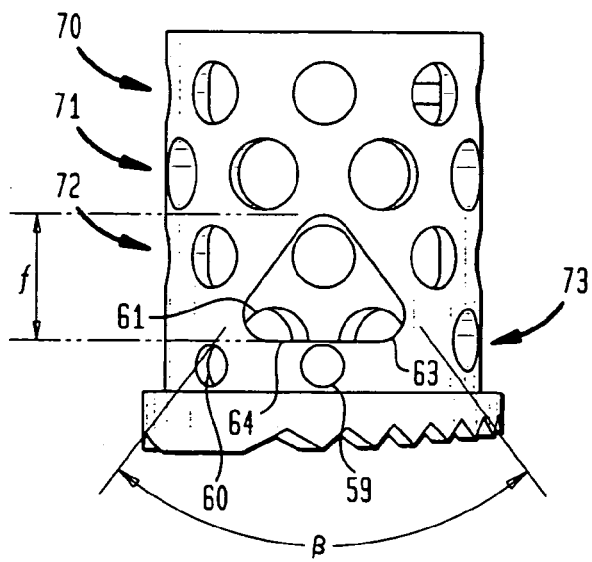
FIG. 6A is a front elevational view of the outer member of the corpectomy device of FIGS. 1-6.

As best seen in FIGS. 6 and 6A, the preferred embodiments include orifices 58 which are preferably arranged in rows around the circumference of member 12 in horizontal planes. The holes 58 in each succeeding row may be staggered in relation to each other. The first row 70 of orifices 58 may be located in wall 42 so that their plane 74 is spaced about 6 mm from upper end 40. Seven holes are equally spaced around wall 42 in row 70, each having a diameter of about 6 mm. Second row 71 has orifices 58 with their plane 74 spaced 14 mm from upper end 40. Eight holes are equally spaced along wall 42 in row 71, each having a diameter of about 7 mm. Row 70 has one fewer holes than row 71, to accommodate the horizontal slit 62 in row 70. The third row 72 has orifices 58 arranged so that the plane 74 is about 22 mm from the upper end 40. Seven holes are arranged in the third row 72, each having a diameter of about 6 mm. Fourth row 73 has orifices 58 arranged so that their plane 74 is spaced about 30 mm from upper end 40. This row has five holes, each having a diameter of about 6 mm. The fourth row 73 only has five holes and third row 72 only has seven rows to accommodate aperture 61. Aperture 61 is substantially triangular in shape, having rounded corners 63 and sides 64. The aperture 61 provides access to chamber 95 so that the device may be packed with bone fragments, bone growth factors, other materials promoting the growth of bone, blood vessels or other tissue, or materials used in the corpectomy procedure. Adjacent sides 64 of aperture 61 define an angle $\beta$ of 70°.

Figure 8:
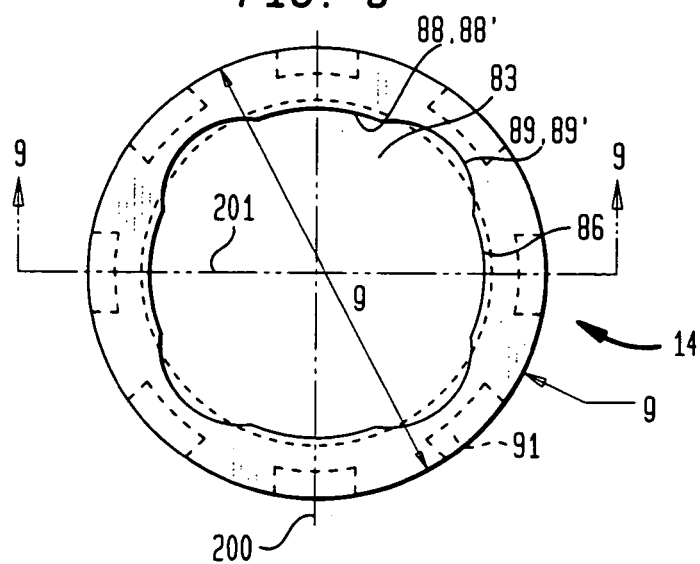
FIG. 8 is a top view of a locking clip of the corpectomy device of FIGS. 1-7.
Figure 9:
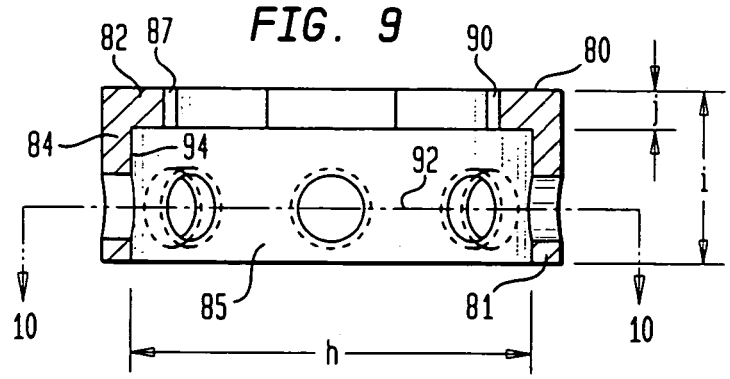
FIG. 9 is a cross-sectional view taken along line 9-9 in FIG. 8.
Figure 10:
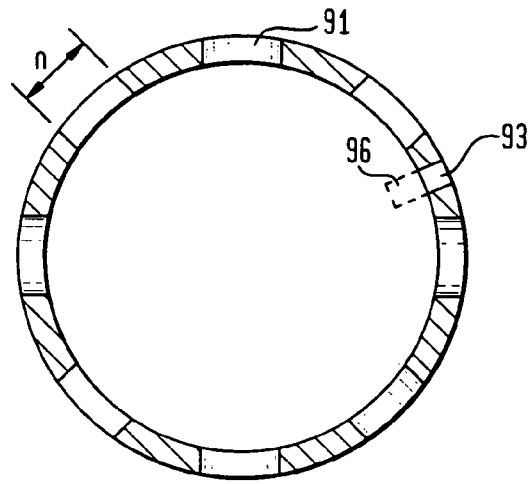
FIG. 10 is a cross-sectional view taken along line 10-10 in FIG. 9.

The preferred locking clip, as best seen in FIGS. 8-10, has a top side 80 and a bottom side 81. The top side 80 of the locking clip 14 comprises a circular disk 82 having an inner surface 87 defining an aperture 83 including surfaces having threads. Extending downwardly from the periphery of circular disk 82 is a wall 84, defining an open side or bore 85 at the bottom side 81 of the locking clip. The locking clip is mounted on surface 40 of outer member 12, as will be described below.

Figure 13:
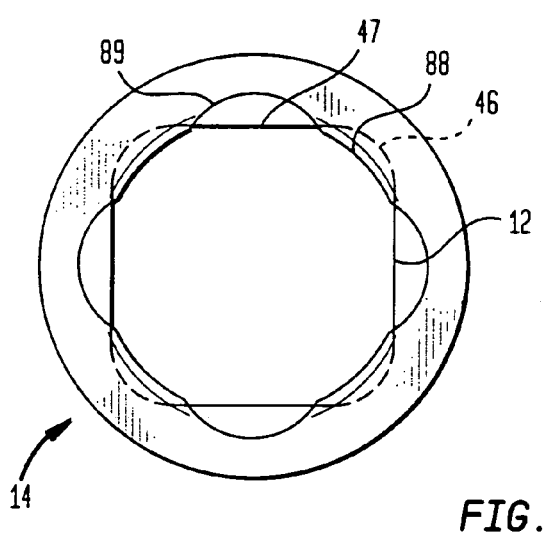
FIG. 13 is a top view of the locking clip and outer cylinder of the corpectomy device of FIGS. 1-12, showing the locking clip in a position in which the inner member is prevented from axial movement with respect to the outer member.

The inner surface includes third surface portions 89' shaped to correspond to the first surface portions 31 on the inner member so that the inner member is telescopingly received in the passage 45 when the locking clip is in its unlocked position shown in FIG. 13. The inner surface 87 also includes fourth surface portions 88'.

Figure 11:
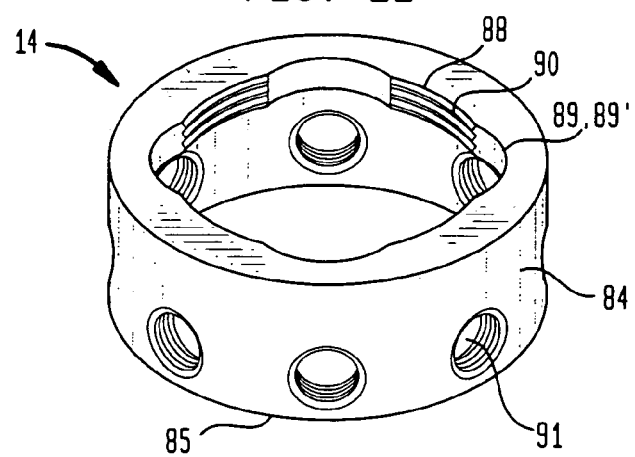
FIG. 11 is a perspective view of the locking clip of the corpectomy device of FIGS. 1-10.
Figure 12:
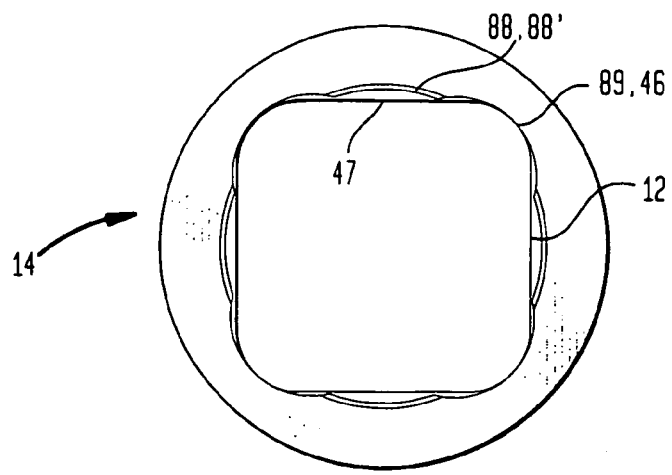
FIG. 12 is a top view of the locking clip and outer member of the corpectomy device of FIGS. 1-11 showing the locking clip in a position which allows movement of the inner member (not shown) to slide.

In the preferred embodiment, aperture 83 has the shape of the rounded square cross-sectional shape of passage 45 intersected with a circle 86. The aperture 83 is defined by surface portions 89' comprising rounded corners and surface portions 88' comprising threaded circular surface segment portions 88 of circle 86. The rounded corners 89 are shaped to correspond to rounded corners 46 of outer member 12 and corners 31 of member 11. Referring to FIG. 11, circular surface portions 88 have threads or ridges 90 extending along surface 87. The threads 90 on circular surface portions 88 engage threads on corner 31 to enable the locking clip to lock the inner member 11 in a position with respect to outer member 12. To accomplish this, locking clip 14 has a locked position and an unlocked position with respect to inner member 11 and outer member 12. FIG. 13 depicts the position of the locking clip with respect to the outer member 12 when locking clip 14 is in its locked position on inner member 18. FIG. 12 depicts the position of the locking clip with respect to member 12 when it is in its unlocked position, thus allowing inner member 18 to slide freely.

Locking clip 14 has a set of bores 91 arranged around the circumference thereof on a common horizontal plane 92. There are eight bores 91 equally spaced along wall 84 of locking clip 14. Each bore 91 has a corresponding orifice 58 in first row 70 on outer member 12. The bores 91 and orifices 58 in first row 70 may be used to further lock the device, as discussed below. Locking clip 14 may also have an orifice 93 for permanently mounting the locking clip 14 on the outer member 12. A pin 96, which is shown in FIG. 10, is mounted in orifice 93 and extends past interior surface 94 of wall 84 and inwardly into slit 62 on outer member 12. The pin 96 rotatably mounts locking clip 14 on the outer member 12 allowing rotation thereon but preventing axial movement. During manufacture, the pin may be welded into place on the locking clip so that the locking clip is pre-mounted on the outer member.

The preferred locking clip 14 has a diameter g of about 34 mm. The open side or bore 85 of locking clip 14 has a diameter h of about 30 mm. The thickness of wall 84 may be about one or two mm. The height i from the top side 80 to the bottom side 81 of the locking clip is about 13 mm. The thickness j of the circular disk 82 is about 3 mm. In the preferred embodiment, the circular surface positions 88 of aperture 83 in disk 82 has 26 mm, or M26×1, left-handed threads corresponding to the threads on member 11. Rounded corners 89 have a radius of about 6 mm, the radius being measured from a point 5.6 mm from an axis 200 and 6.5 mm from an axis 201 in FIG. 8. Bores 91 are arranged on plane 92 so that the plane is spaced 9 mm from top side 80. Preferably, bores 91 have a diameter of about 6 mm and are threaded to receive screws. Orifice 93 has a diameter of about 2 mm.

The locking clip 14 is mounted on the outer member 12 by placing the locking clip 14 on the outer member 12 so that the upper end 40 of the outer cylinder is received in the open side or bore 85 of the locking clip. A pin is then mounted in orifice 93 or attached to the inner surface 94 of the locking clip so that the pin extends into slit 62. Locking clip 14 is mounted on the outer member 12 and is rotatable thereon so that locking clip 14 has a locked position and an unlocked position. FIGS. 12 and 13 illustrate a top view of the locking clip mounted on the outer member. In FIG. 12, the assembly is shown so that the locking clip 14 is its unlocked position. In this position, the pin in slit 62 is adjacent side 78 or side 76 of slot 62. Whether side 76 or 78 is the unlocked position is a matter of design choice. Inner member 11 may then be inserted into passage 45 so that bottom end 16 is received in the passage. When the locking clip 14 is in the unlocked position, rounded corners 89 of the locking clip are aligned with rounded corners 46 of the outer member 12. Circular surface portions 88, which have ridges or threads 90, are then aligned with sides 47 of the outer member 12. When the locking clip is in a locked position, the pin in slit 62 is adjacent the other of sides 78 and 76. As shown in FIG. 13, rounded corners 89 are aligned with sides 47 when the locking clip is in the locked position.

Figure 13A:
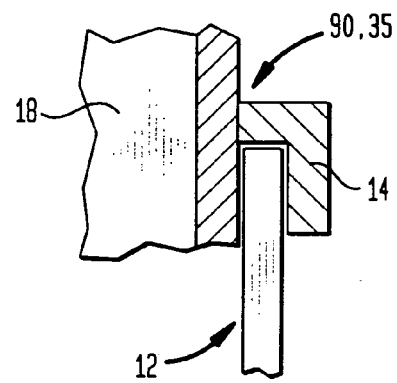
FIG. 13A is a partial cross-sectional view taken along line 13A-13A in FIG. 1.
Figure 14:
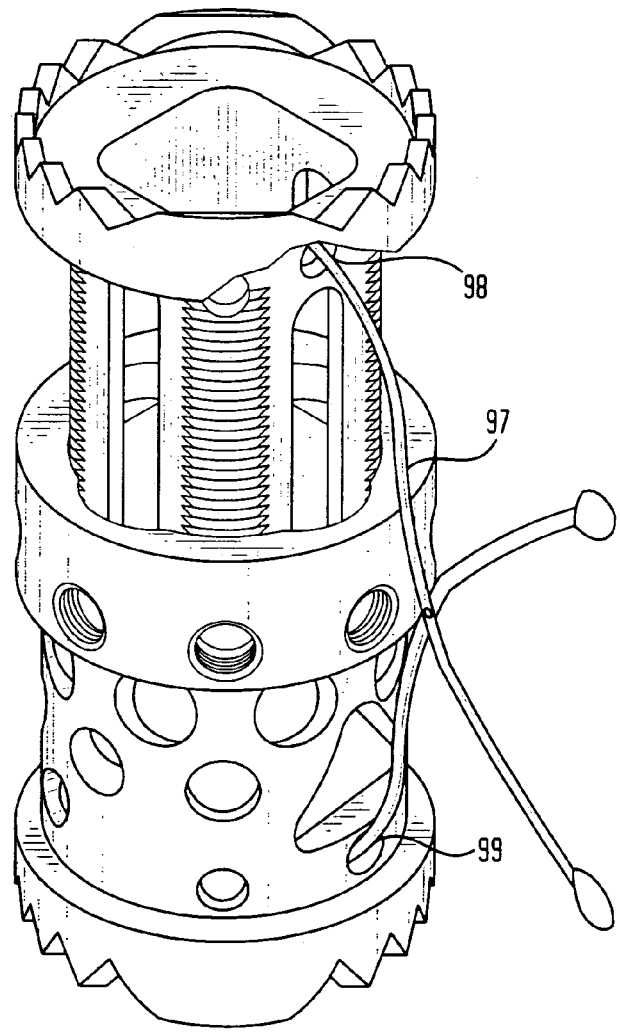
FIG. 14 is a schematic, perspective view of a corpectomy device in accordance with the embodiments of FIGS. 1-13A and a distractor for installing the corpectomy device.

To assemble the device, the bottom end 16 of inner member 11 is inserted through aperture 83 and into the passage 45 of outer member 12. When the inner member has been inserted into passage 45, passage 45 and hollow space 30 form a chamber 95. In order to insert the inner member into passage 45, rounded corners 46 on the outer member must be aligned with rounded corners 89 on the locking clip 14 so that locking clip 14 is its unlocked position. When the locking clip is moved to its locked position, circular surface portions 88 having threads or ridges 90, overlap rounded corners 46 and engage the ridges or threads 35 on the rounded corners 31 of inner member 11. FIG. 13A illustrates the engaging threads of clip 14 and member 11. In this position, the relative position of the inner member 11 is axially fixed with respect to the outer member 12. The position of the locking clip 14 is fixed in this locked position by inserting one or more screws into bores 91 so that the screws extend into orifices 58 in first row 70 on the outer member 12. If the locking clip is not premounted on the outer member prior to insertion of member 11, the locking clip 14 will be placed on end 40 of the outer member 12 and pin 96 may be mounted in hole 93 of the locking clip, extending into slot 62.

The length of slit 62 is approximately equal to the horizontal dimension of the rounded corners 31. These dimensions are desirable so that the locking clip is prevented from rotating beyond its locked position and the ridges or threads 90 and 35 are prevented from coming out of engagement with each other by rotating the locking clip too far beyond its locked position. Thus, when the locking clip is in its locked position, the pin 96 mounted on the locking clip is abutted against one of the first side 78 or second side 76. Likewise, when the locking clip is moved into its unlocked position so that rounded corners 31 are aligned with rounded corners 89, the pin 96 mounted to the locking clip 14 is abutted against the other of the first side 78 or second side 76.

To use the corpectomy device, the locking clip is mounted on outer member 12 and is initially in its unlocked position and the inner member is assembled with the outer member and locking clip. The passage 45 is filled by the surgeon with bone material, bone growth factors, bone morphogenic proteins (BMP's), or other materials for encouraging bone growth or growth of other tissue through the many apertures provided in the device. The device is distracted by inserting one end 98 of a distractor or distraction device 97 into holes 38 and/or 39 and the other end 99 of the distractor into holes 59 and/or 60 and separating the ends of the distractor so that the inner member 11 is drawn upwardly and away from the outer member 12 to the desired overall height. The locking clip 14 is then rotated to the locked position and one or more set screws are inserted into the bores 91 to fix the position of the locking clip with respect to the outer member. The one or more set screws prevent the locking clip 14 from rotating. Thus, the corpectomy device may be distracted in situ and conveniently locked in position so that the device may be adjusted to the height required to replace a removed vertebra and support the spine. Bone cement is not required to lock the device, but may be used. Preferably, the device is tapped with a hammer so that the teeth on top flange 21 and lower flange 50 engage the adjacent vertebrae.

The inner member 11, outer member 12, locking clip 14 and any set screws are preferably comprised of titanium but may also be comprised of stainless steel, ceramics, composite materials, other materials known in the surgical and medical arts, and/or biologically inert materials may be used. The orifices 58, aperture 61, apertures 26 and 52, and orifices 33 may have any shape. Curvilinear shapes are preferred, however, for ease of manufacture. The device must also support the patient's spine and corners create increased regions of stress in the device. The elongated orifices 33 in inner member 11 are preferred so that after the device is distracted, the surgeon can pack additional bone material, or other material desired, into the device. In addition, the relatively large aperture 61 is convenient for packing the device with such materials.

The cross-sectional shapes of the part 18, hollow space 30, outer surface 43 of outer member 12, passage 45 and aperture 83 may have any shape which allows the inner member to be slidably received in passage 45 and allows locking clip 14 to engage the inner and outer members to lock the relative position of the inner member with respect to the outer member. For example, the part 18, passage 45 and aperture 83 may have shapes including a triangle, pentagon or octagon. It is also preferred that the inner member does not rotate with respect to the outer member 12. The locking clip and inner member may engage one another in a number of ways. For example, the engaging elements 90 and 35 discussed above may comprise ridges, threads or grooves formed on rounded corners 31 of part 18 and circular surface portions 88 of locking clip 14. Preferably, the threads, grooves, or ridges are disposed along a horizontal straight line, for ease of manufacture. If it is desirable that the position of the inner member 11 is adjusted either upwardly or downwardly as the locking clip 14 is moved to its locked position, the ridges 90 and 35 may comprise threads which are slightly angled in a vertical direction. Alternatively, circular surface portions 88 may have depressions and rounded corners 31 may have ridges which are engaged in the depressions.

The particular dimensions of the device discussed above are dimensions for that particular embodiment only. Use of the corpectomy device in the spines of different patients, and in different positions along the spine, will require variations in the dimensions. Thus, a variety of devices having different heights and diameters may address different applications and the preferences of different surgeons. The particular angle for the top and lower flanges will also vary according the particular application and the surgeon's preference. The flanges may be angled anywhere from 0° to 8° or much greater to restore the curvature of the spine. The particular dimensions are not critical to the invention. In one variation, the teeth 28 and 55 may be replaced by, or used in addition to, screws anchoring the device to adjacent vertebrae. Holes may be provided in the top flange and lower flange for insertion of the screws, which can engage adjacent vertebrae.

Figure 15:
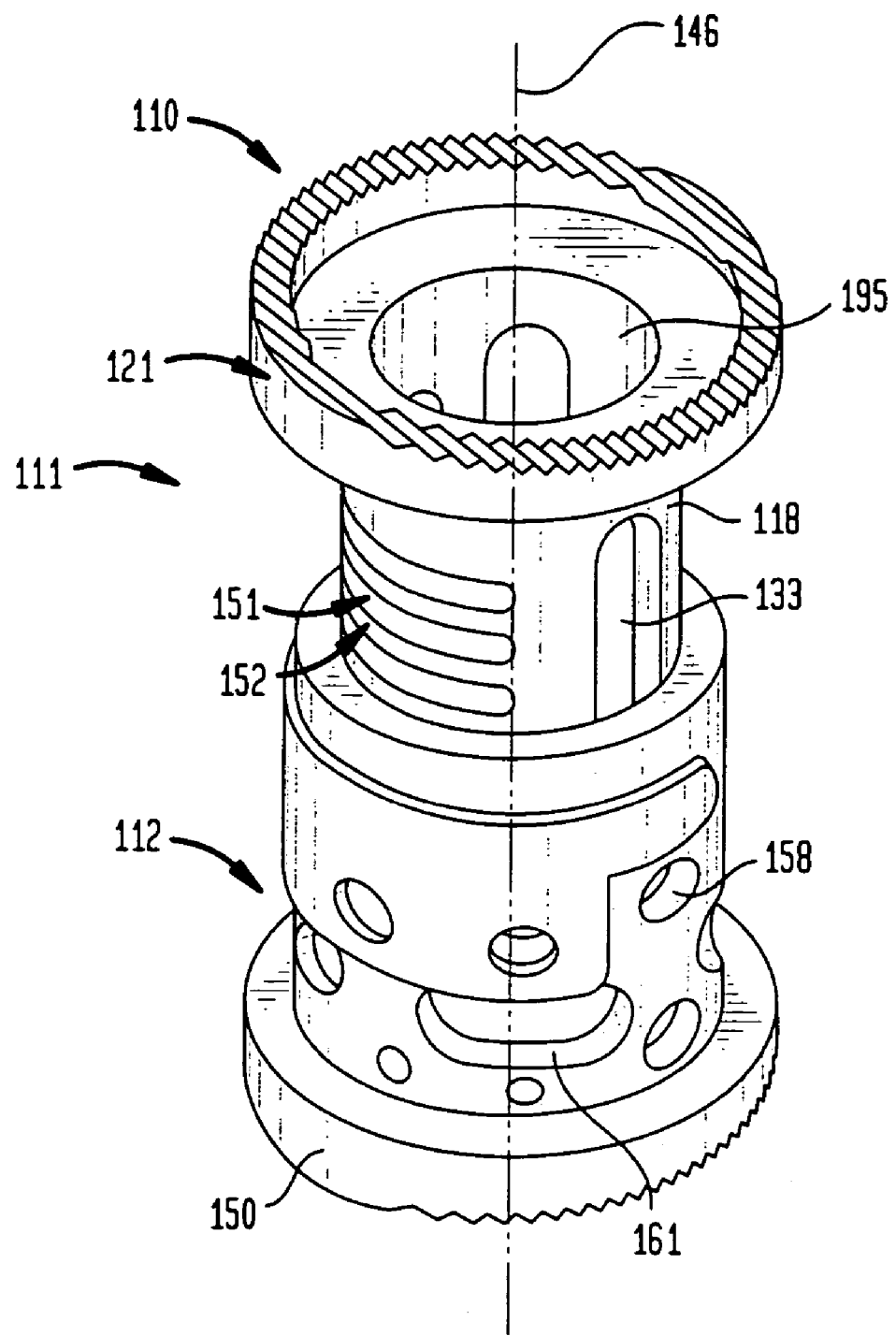
FIG. 15 is a perspective view of a corpectomy device in accordance with another embodiment of the invention.
Figure 16:
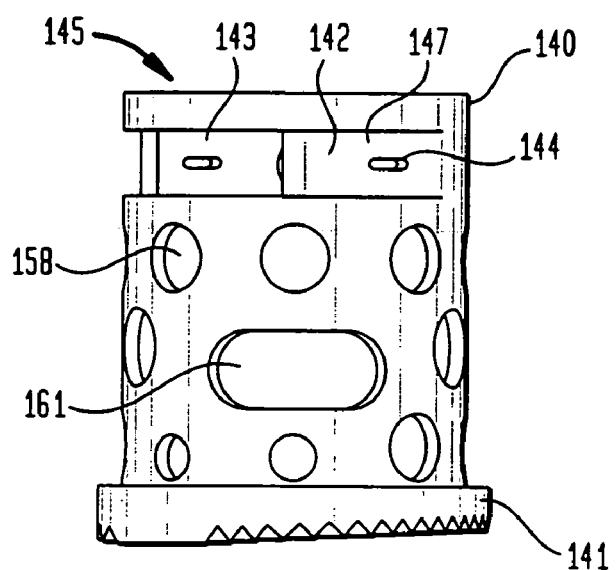
FIG. 16 is a front elevational view of an outer cylinder of the embodiment of FIG. 15.
Figure 17:
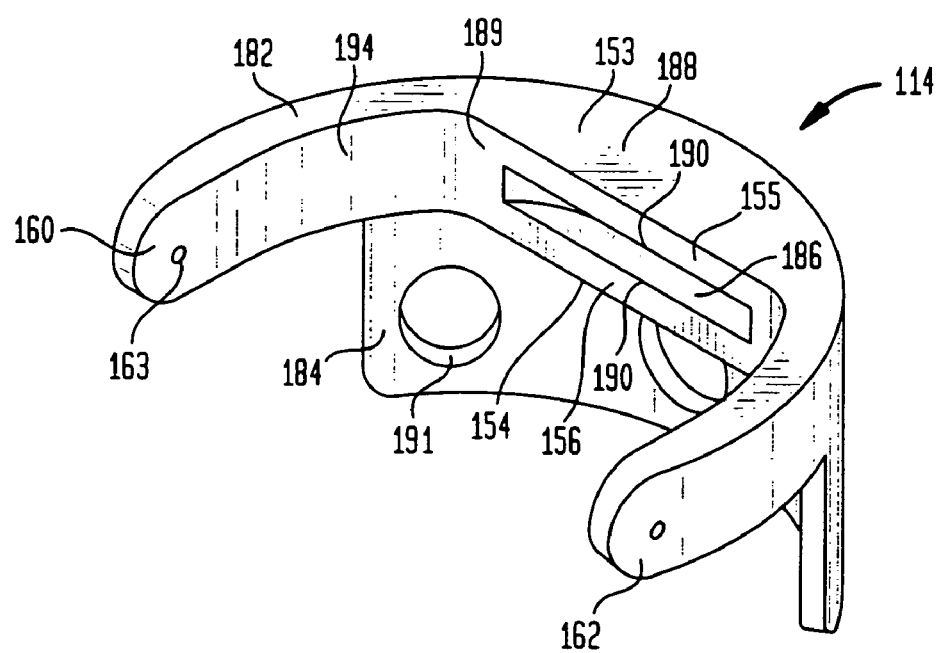
FIG. 17 is a perspective view of a locking clip in accordance with the embodiment of FIGS. 15-16.

Another embodiment of the invention is illustrated in FIGS. 15-17. In this embodiment, inner member 111 is slidably received in outer member 112, which have interengaging circular cross-sectional shapes and a common longitudinal axis 146. Inner member 111 preferably has a flange 121 at outer axial end of the member, the flange 121 has teeth for engaging an adjacent vertebra. The inner member includes a tubular part 118 extending from flange 121. The inner member 111 has a series of apertures or slots 151 defining circumferential bridges 152 therebetween. Orifices 133 similar to orifices 33 are provided in the part 118.

The outer member 112 has orifices 158. Orifices 158 and 133 may be the same or similar to the orifices described in reference to the preferred embodiment above. The outer member 112 has an upper end 140 and a lower end 141, a hole 143 extends through the outer member 112 to chamber 195 defined by inner and outer members. Notches 142 are formed in the outer cylinder 112, on either side of hole 143 for interaction with locking clip 114. Notches 142 have walls 147 in which holes 144 are formed, one in each notch for mounting the locking clip 114 on the outer member 112. The outer member 112 preferably includes an aperture 161, which may have the elongated shape shown in FIGS. 15 and 16, or may have the shape of aperture 61 discussed above.

The locking clip 114 of this embodiment has the shape of a portion of a cylinder and is sized and shaped to be mounted on an outer surface of the outer member 112, which has a circular cross-section in this embodiment. Locking clip 114 has a curved wall 184 extending downwardly from a curved arm piece 182. The arm piece 182 has an inner surface 194 and a wedge portion 188 having a straight face 189 extends inwardly from the arm piece 182. The wall 184 has apertures 191 which correspond to a first row of orifices formed in the outer cylinder 112 similarly to the first row 70 of orifices 58 discussed above.

On the inner face 189 of the wedge portion 188, a depression 186 is formed having side walls 190 extending horizontally into wedge portion 188. Arm 182 has a first end 160 and second end 162 on either side of the wedge portion 188. The locking clip includes pins 163 on the inner surface 194 adjacent ends 160 and 162. The wedge portion 188 includes a top surface 153 and bottom surface 154. Depression 186 defines portions 155 and 156 in inner surface 189 on either side of depression 186.

The notches 142 on the outer cylinder 112 receive the ends 160 and 162 of arm 182. Locking clip 114 is mounted on outer cylinder 112 in notches 142 so that the pins 163 are received in the holes 144 on the outer cylinder. Holes 144 are elongated in a horizontal direction. Holes 144 each have a first side and a second side. When the locking clip 114 is mounted on outer cylinder 112, the depression 186 in the wedge portion 188 is disposed in aperture 143 in the outer cylinder but does not protrude into passageway 145. The depression 186 is open to the passage 145 in outer cylinder 112. The locking clip is preferably pre-mounted on the outer cylinder 112, but may be snapped into place when the device is installed.

Locking clip 114 has an unlocked position, in which pins 163 abut one side of the holes 144. The inner member 111 may be inserted into passageway 145 when the locking clip is in its unlocked position because wedge portion 188 does not protrude through aperture 143 into passageway 145. Locking clip 114 also has a locked position in which pins 163 abut the other sides of the holes 144. In this position, the wedge portion 188 protrudes into the aperture 143 and wedge portion 188 is located in passageway 145. After the inner cylinder 111 has been inserted into passageway 145, locking clip 114 may be translated into its locked position. The locking clip is moved into its locked position by translating the clip 114 in a direction transverse to the longitudinal axis 146. In its locked position, the depression 186 on the locking clip engages an bridge 152 on the inner cylinder. When the locking clip 114 is moved to its locked position, bridge 152 is received in depression 186, and portions 155 and 156 on the face 189 are received in holes 151 adjacent the particular bridge 152 engaged by depression 186 in the locking clip.

As will be readily appreciated, numerous other variations and combinations of the features discussed above will be employed without departing from the present invention. Accordingly, the foregoing description of certain preferred embodiments should be taken by way of illustration, rather than by way of limitation, of the features discussed above.

The invention claimed is:

1. A corpectomy device, comprising:
   an outer tubular member having a longitudinal axis and a passage;
   an inner tubular member that is axially moveable with respect to said longitudinal axis and non-rotatable in said passage of said outer member, said inner member defining a chamber with said outer member; and
   a locking clip engagable with said outer member and said inner member and moveable between an unlocked position and a locked position for locking said outer member and said inner member in a relative axial position with respect to one another, said locking clip having an inner surface including a first longitudinally extending surface portion and a second longitudinally extending surface portion, at least said second surface portion being curvilinear, and said first surface portion being spaced further from said longitudinal axis than said second surface portions wherein an outer surface of said inner member defines a polygonal cross-sectional shape, including sides and corners and wherein said unlocked position is defined by said corners of said inner member being aligned with said first surface portions of said locking clip, thus facilitating axial movement of said inner member with respect to said outer member.

2. The corpectomy device of claim 1, wherein said second surface portions on said locking clip and said corners on said inner tubular member include overlapping ridges, the interaction of which facilitates locking said inner tubular member and said outer tubular member in a relative axial position with respect to one another, thus defining said locked position of said locking clip.

3. The corpectomy device of claim 2, wherein said locking clip is rotatable relative to said inner and said outer members between said locked and said unlocked positions.

4. The corpectomy device of claim 1, wherein said locking clip has a bore and said outer member has a corresponding hole, said bore and hole being engageable by a screw for maintaining said locking clip in said locked position.

5. A corpectomy device comprising:

an outer tubular member defining an interior passageway extending along a longitudinal axis, said outer member having a first bone contacting end and a second end;

an inner member slidably received in said passageway and having a first bone contacting end and a second end for insertion into said outer member second end, and an outer surface of said inner member having a plurality of radially extending locking elements; and a locking clip having a plurality of locking elements engageable with said inner member locking elements extending into said passageway, said locking clip being rotationally mounted on said second end of said outer member and rotatable from a first position where said locking elements are circumferentially spaced from one another to a second position where said locking elements engage one another to prevent relative axial movement of said inner and outer members wherein said locking clip has a first part surrounding an outer surface of said outer member and a second part overlying said second end of said outer tubular member and extending over said passageway thereof wherein said second part of said locking clip has first and second inner circumferential surface portions with said first surface portion being spaced further from said longitudinal axis of said passageway then said second surface portion wherein only said second inner surface portions of said clip include said locking elements engageable with said locking elements of said inner member.

* * * * *

UNITED STATES PATENT AND TRADEMARK OFFICE
CERTIFICATE OF CORRECTION

PATENT NO. : 7,648,529 B2  Page 1 of 1
APPLICATION NO. : 11/010496
DATED : January 19, 2010
INVENTOR(S) : An et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1436 days.

Signed and Sealed this

Twenty-eighth Day of December, 2010

David J. Kappos
*Director of the United States Patent and Trademark Office*